United States Patent
Fries et al.

(10) Patent No.: US 6,836,953 B2
(45) Date of Patent: Jan. 4, 2005

(54) METHOD OF PRODUCING A BIOMETRIC SENSOR

(75) Inventors: Manfred Fries, Hunderdorf (DE); Thomas Münch, Laaber (DE); Reinhard Fischbach, Regensburg (DE)

(73) Assignee: Infineon Technologies AG, Munich (DE)

( * ) Notice: Subject to any disclaimer, the term of this patent is extended or adjusted under 35 U.S.C. 154(b) by 226 days.

(21) Appl. No.: 10/289,087

(22) Filed: Nov. 6, 2002

(65) Prior Publication Data

US 2003/0062621 A1 Apr. 3, 2003

Related U.S. Application Data

(62) Division of application No. 09/761,806, filed on Jan. 16, 2001, now Pat. No. 6,528,723, which is a continuation of application No. PCT/DE99/02146, filed on Jul. 12, 1999.

(30) Foreign Application Priority Data

Jul. 14, 1998 (DE) .......................................... 198 31 570

(51) Int. Cl.[7] ................................................ H01S 4/00
(52) U.S. Cl. ........................ 29/592.1; 29/825; 29/832; 438/116; 438/123
(58) Field of Search ............................... 29/592.1, 825, 29/832; 438/116, 123

(56) References Cited

U.S. PATENT DOCUMENTS

| | | | | |
|---|---|---|---|---|
| 4,429,413 A | | 1/1984 | Edwards | |
| 5,051,802 A | * | 9/1991 | Prost et al. | 257/434 |
| 5,122,862 A | * | 6/1992 | Kajihara et al. | 257/704 |
| 5,138,145 A | * | 8/1992 | Nakamura et al. | 250/208.1 |
| 5,483,100 A | | 1/1996 | Marrs et al. | |
| 5,773,323 A | * | 6/1998 | Hur | 438/123 |
| 5,862,248 A | | 1/1999 | Salatino et al. | |
| 5,887,343 A | | 3/1999 | Salatino et al. | |
| 5,956,415 A | | 9/1999 | McCalley et al. | |
| 6,307,258 B1 | | 10/2001 | Crane, Jr. et al. | |
| 6,528,723 B2 | * | 3/2003 | Fries et al. | 174/52.4 |

FOREIGN PATENT DOCUMENTS

| | | |
|---|---|---|
| DE | 196 34 849 A1 | 3/1998 |
| EP | 0 786 745 A2 | 7/1997 |
| EP | 0 789 334 A2 | 8/1997 |
| FR | 2 736 179 | 1/1997 |

\* cited by examiner

*Primary Examiner*—Carl J. Arbes
(74) *Attorney, Agent, or Firm*—Laurence A. Greenberg; Werner H. Stemer; Ralph E. Locher

(57) ABSTRACT

In a biometric sensor and a method for its production, a sensor chip is provided with connecting contacts in the form of electrically conductive bumps. The sensor chip is inserted into a chip housing, the bumps making contact with corresponding connecting leads belonging to the chip housing. At the same time as this contact is made, the sensor chip is bonded adhesively into the chip housing by an adhesive layer, which surrounds the sensor field in a sealing manner.

4 Claims, 2 Drawing Sheets

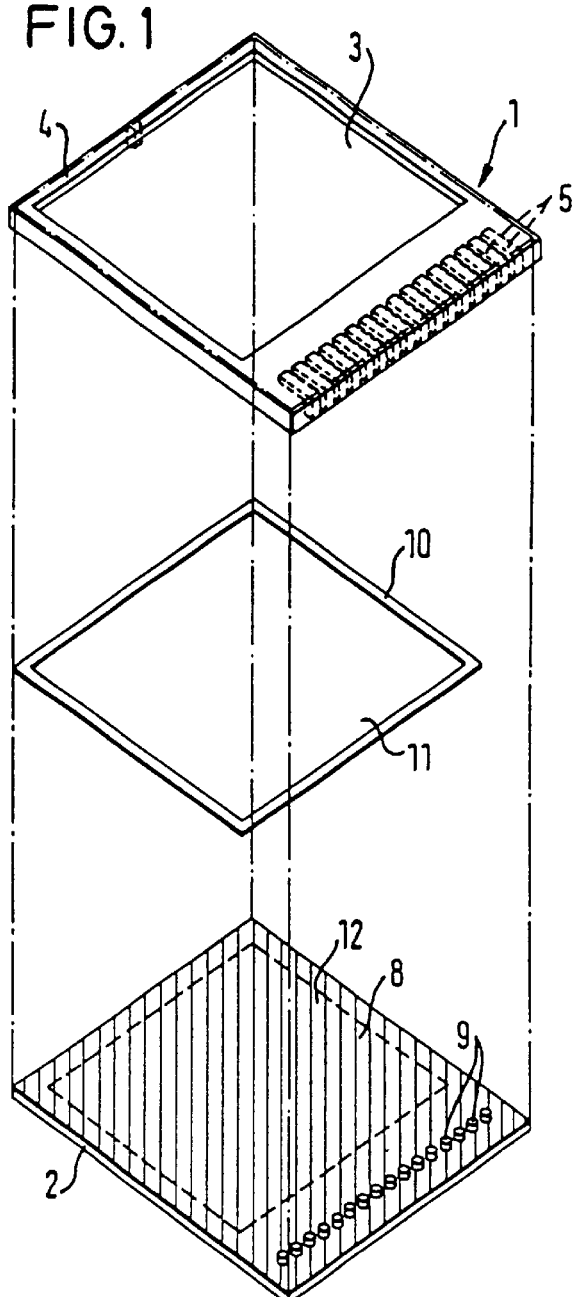
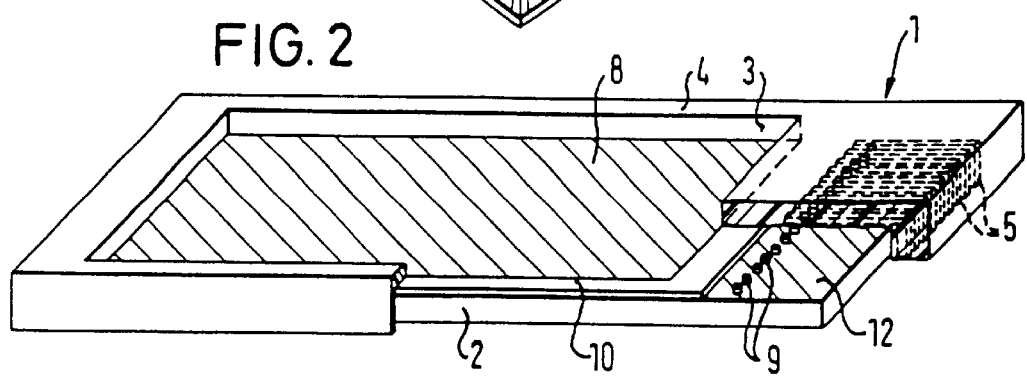

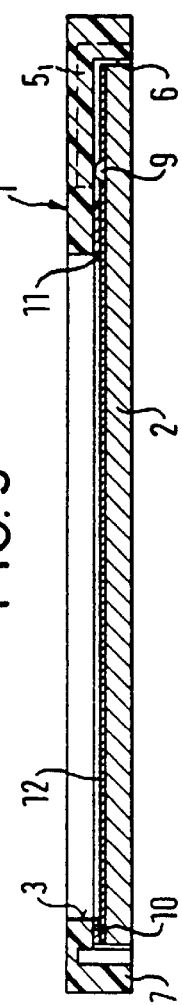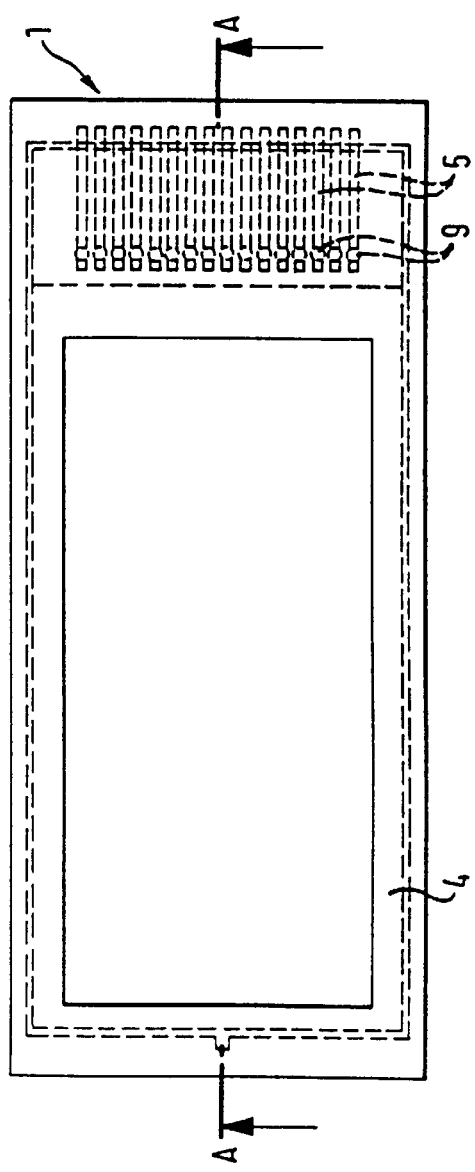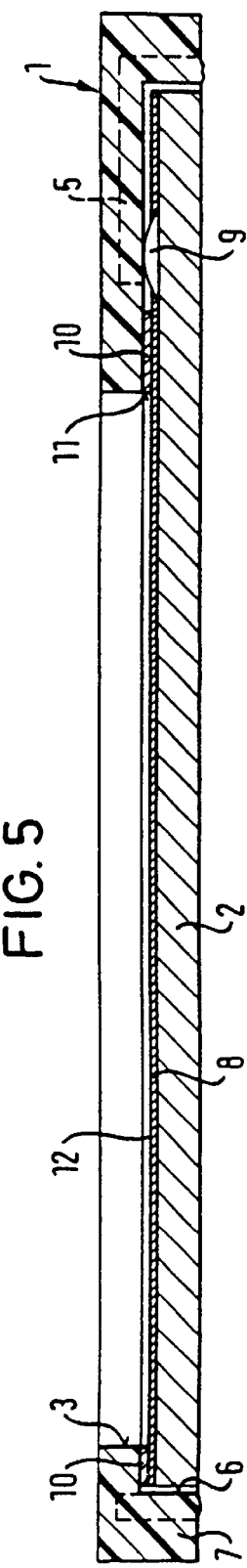

METHOD OF PRODUCING A BIOMETRIC SENSOR

CROSS-REFERENCE TO RELATED APPLICATION

This is a division of U.S. application Ser. No. 09/761,806, filed Jan. 16, 2001, now U.S. Pat. No. 6,528,723, issued Mar. 4, 2003 which was a continuation of International Application PCT/DE99/02146, filed Jul. 12, 1999, which designated the United States and which was not published in English.

BACKGROUND OF THE INVENTION

Field of the Invention

The invention relates to a method of producing a biometric sensor having a sensor chip and a chip housing, into which the sensor chip is inserted.

It is known to record features specific to a person, for example finger minutiae, that is to say fingerprints, for the authentication of persons. Such an authentication of persons can be used, for example, in mobile telephones, computers, motor vehicles, keys, etc. In certain fields of application, in particular in mobile telephones, it is necessary to configure the chip housing to be as small as possible, in order to permit incorporation. In particular, in this case a minimum component thickness is desirable. Published, European Patent Application EP 0 789 334 A2 discloses a biometric sensor in which a sensor chip is fitted to a leadframe. The sensor chip has an electrical contact made with it by a wire-bonding method and, by a molding compound is encapsulated in such a way that the sensor surface is accessible through an appropriate cutout in the molding compound. The disadvantage in this known sensor is that, first, it is still relatively large and, second, it is relatively complicated to produce.

SUMMARY OF THE INVENTION

It is accordingly an object of the invention to provide a method of producing a biometric sensor that overcomes the above-mentioned disadvantages of the prior art devices and methods of this general type, which has the lowest possible size and is simple to fabricate.

With the foregoing and other objects in view there is provided, in accordance with the invention, a biometric sensor. The biometric sensor contains a housing, connecting leads disposed on or in the housing, and a sensor chip disposed in the housing. The sensor chip has a top, a field sensor, and connecting contacts in a form of electrically conductive bumps, the electrically conductive bumps making contact with the connecting leads and have a given height. A scratch protection covering is disposed on the top of the sensor chip. An adhesive layer is disposed between the scratch protection covering and the housing. The adhesive layer is disposed at least around the sensor field, the adhesive layer has a thickness matched to the given height of the electrically conductive bumps creating a leak-tight connection between the sensor chip and housing.

It is characteristic of the biometric sensor according to the invention that the chip housing already has connecting contacts for the sensor chip at predetermined points. When it is inserted into the chip housing with the bumps (knob-like elevations of conductive material) located at appropriate points, the chip is automatically brought into connection with the connecting contacts belonging to the chip housing, so that subsequent wire bonding is dispensed with completely. The sensor chip is seated firmly and tightly in the chip housing, so that it is also possible to dispense completely with the molding, that is to say the encapsulation of the chip with a plastic compound. Furthermore, the biometric sensor according to the invention can be produced in a very simple, quick and low-waste manner. A particular advantage in this case is that contact making between the bumps and the connecting contacts belonging to the chip housing, and sealing between the chip housing and the sensor chip by the adhesive layer are carried out in one operation. Since the sensor chip according to the invention does not have to be encapsulated from both sides either, and the separate chip housing can be matched exactly to the geometry of the sensor chip and the subsequent field of use of the sensor, the sensor according to the invention can also be made significantly smaller than previously conventional sensors, given a predefined sensor surface.

According to an advantageous embodiment, in addition to the bumps in contact with the connecting leads, at least one further supporting bump is provided on the top of the sensor chip at a point which prevents the sensor chip from tilting relative to the chip housing. A "dummy bump" of this type ensures that the sensor chip, after being inserted into the corresponding depression in the chip housing, is aligned in the same plane as the chip housing. This ensures a satisfactory contact between all the bumps on the sensor chip and the corresponding connecting contacts belonging to the chip-housing connecting leads.

The adhesive layer expediently is formed of a frame-like circumferential adhesive film that is applied around the sensor surface of the sensor chip.

According to an advantageous embodiment, the chip housing is an injection-molded housing, the connecting leads being embedded in the material of the chip housing and being routed to an outer edge of the chip housing. This permits subsequent damage to the connecting leads to be avoided. The connecting leads emerging at the outer edge of the chip housing form the leads or pins, which can be configured as plug-in, solder-in or clamp contacts.

With the foregoing and other objects in view there is further provided, in accordance with the invention, a method of producing a biometric sensor. The method includes the steps of:

a) providing a water having sensor chips with connecting contacts;

b) applying conductive bumps to the connecting contacts of the sensor chips;

c) covering a front side of the wafer with a scratch protection covering;

d) removing the scratch protection covering from over a top of the conductive bumps;

e) separating the sensor chips from one another;

f) applying an adhesive layer around a sensor field of a respective sensor chip, the adhesive layer having a thickness being matched to a height of the conductive bumps such that, in a subsequent method step, a leak-tight connection between the sensor chip and a chip housing is created;

g) introducing the sensor chip into the chip housing, the chip housing having electrical connecting leads disposed one of in and on the chip housing; and h) carrying out simultaneously an adhesive bonding of the respective sensor chip to the chip housing and making contact between the conductive bumps and the electrical connecting leads belonging to the chip housing.

It is therefore characteristic of the method according to the invention that, as early as during the wafer production process, appropriate bumps, that is to say knob-like conductive elevations, are applied to the sensor-chip connecting contacts of the wafer. This can be carried out, for example, by screen printing. The top (front side) of the wafer is subsequently provided with a preferably transparent scratch protection covering, whose layer thickness is matched to the bump height. The bumps are then freed from the scratch protection covering and any oxide layer that may be present, preferably by using a chemical mechanical polishing process (CMP). At the same time, this step achieves equalization of the bumps, that is to say coplanarity between the bumps is produced, which improves the ability to make contact in the subsequent processes. Following the separation of the sensor chips, an adhesive medium, preferably an adhesive film, is applied around the sensor surface, its thickness being matched to the bump height. The sensor chip is then mounted in a housing corresponding to the product requirements, preferably in an injection-molded plastic housing, the adhesive bonding of the sensor chip to the chip housing and the making of electrical contact between bumps and chip housing being carried out in one step.

In the method according to the invention, therefore, the equalization of the bumps to achieve coplanarity and the removal of the protective layer and the oxide layer is carried out at the wafer level. Making contact between the bumps and the chip housing, and sealing between the chip housing and sensor chip are carried out in a single operation. In this way, the sensor can be produced in a very simple and cost-effective manner and with very small dimensions.

As an alternative to the method in which the entire front side of the wafer is covered with a scratch protection covering, and the scratch protection covering is subsequently removed again from the top of the bumps, it is also possible to apply the scratch protection covering to the front side of the wafer in such a way that, by suitable masking in the area of the bumps, openings in the scratch protection covering are kept free, the mask subsequently being removed again.

Other features which are considered as characteristic for the invention are set forth in the appended claims.

Although the invention is illustrated and described herein as embodied in a method of producing a biometric sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, exploded, perspective view of a biometric sensor according to the invention;

FIG. 2 is a partially cut-away, perspective view of the sensor;

FIG. 3 is a longitudinal sectional view of the sensor of FIG. 2 taken along the line III—III shown in FIG. 4;

FIG. 4 is a plan view of the sensor; and

FIG. 5 is an enlarged, longitudinal sectional view of the sensor from FIG. 2.

DESCRIPTION OF THE PREFERRED EMBODIMENTS

In all the figures of the drawing, sub-features and integral parts that correspond to one another bear the same reference symbol in each case. Referring now to the figures of the drawing in detail and first, particularly, to FIG. 1 thereof, there is shown a biometric sensor which essentially contains a chip housing 1 and a sensor chip 2.

The chip housing 1 includes an injection-molded plastic housing which is rectangular from a plan view. A likewise rectangular, continuous cutout 3 in the chip housing 1 has a size such that a front part of a finger, on which the minutiae are located, can be placed on it. In addition, the cutout 3 is dimensioned such that, in a front edge area and in both lateral edge areas, there is only a narrow web 4. A rear edge area of the chip housing 1 is wider and has a large number of connecting leads 5 which are located beside one another and already integrated in the chip housing 1. The connecting leads 5 run on an underside of the chip housing 1 in the exemplary embodiment shown, but can also be embedded completely in the housing material, so that only their front and rear ends are exposed for the purpose of making contact.

Formed in the chip housing 1 from the underside is a central depression 6 (FIG. 3), so that a downwardly projecting, circumferential, narrow rim 7 is formed, which completely encloses the inserted sensor chip 2 at the sides. In the inserted state, an underside of the sensor chip 2 runs in alignment with the underside of the circumferential rim 7. As can be seen, a width of the rim 7 is relatively narrow, even at a front and rear end of the chip housing 1, so that the overall length of the chip housing 1 is only a little longer than that of the sensor chip 2.

The sensor chip 2 has a rectangular sensor field 8, whose size corresponds approximately to that of the cutout 3 in the chip housing 1 (FIG. 2). When the sensor chip 2 is inserted, the sensor field 8 is aligned with the cutout 3 in the chip housing 1, so that the maximum sensor-field area can be used to evaluate the minutiae of a finger placed on it.

Connecting leads leading away from the sensor field 8 end on a top of the sensor chip 2 in a large number of connecting contacts which are located beside one another in a row and are configured in the form of electrically conductive bumps 9, that is to say knob-like elevations. The bumps 9 can be applied to the wafer by screen printing, for example. In addition, the bumps 9 are disposed in such a way that when the sensor chip 2 is inserted, each bump 9 comes into contact with an associated connecting lead 5 belonging to the chip housing 1, which produces an electrical connection with the connecting lines 5.

Also located on the top of the sensor chip 2 is a transparent scratch protection covering 12 which is illustrated hatched in FIGS. 1 and 2 and which has already been applied to the entire area of the sensor chip 2 during the wafer production. A height of the scratch protection covering 12 is matched to the height of the bumps 9. Furthermore, the scratch protection covering 12 and any oxide layer which may be present have been removed again from the top side of the bumps 9, for example by a chemical mechanical polishing process, so that an electrically conductive connection can be produced between the bumps 9 and the connecting leads 5.

In order to avoid tilting of the sensor chip 2 within the chip housing 1 during assembly, supporting bumps can be provided in the front end area of the sensor chip 2, the bumps corresponding to the bumps 9 but having only a supporting function and no electrical conducting function.

An adhesive layer 10 in the form of a frame-like adhesive film is applied to the sensor chip 2 separated from the wafer or to the scratch protection covering 12 (FIGS. 1 and 5). A central clearance 11 in the adhesive layer 10 corresponds to the size of the sensor field 8 or to that of the chip-housing cutout 3. In addition, the thickness of the adhesive layer 10 is matched to the height of the bumps 9. The adhesive layer 10 serves to stick the sensor chip 2 into the chip housing 1. At the same time, the adhesive layer 10 creates a circumferential sealing frame that ensures a circumferential, leak-tight connection between the chip housing 1 and the sensor chip 2.

When the sensor chip 2 is inserted into the depression 6 in the chip housing 1 for the purpose of adhesive bonding, the making of direct electrical contact between the bumps 9 and the connecting leads 5 belonging to the chip housing 1, and also the sealing between sensor chip 2 and chip housing 1 are carried out simultaneously.

We claim:

1. A method of producing a biometric sensor, which comprises the steps of:

providing a wafer having sensor chips with connecting contacts;

applying conductive bumps to the connecting contacts of the sensor chips;

covering a front side of the wafer with a scratch protection covering;

removing the scratch protection covering from over a top of the conductive bumps;

separating the sensor chips from one another;

applying an adhesive layer around a sensor field of a respective sensor chip, the adhesive layer having a thickness being matched to a height of the conductive bumps such that, in a subsequent method step, a leak-tight connection between the sensor chip and a chip housing is created;

introducing the sensor chip into the chip housing, the chip housing having electrical connecting leads disposed one of in and on the chip housing; and carrying out simultaneously an adhesive bonding of the respective sensor chip to the chip housing and making contact between the conductive bumps and the electrical connecting leads belonging to the chip housing.

2. The method according to claim 1, which comprises removing the scratch protection covering from the top of the conductive bumps by using a chemical mechanical polishing process.

3. The method according to claim 1, which comprises exposing the tops of the conductive bumps such that all exposed bump tops lie in a same plane.

4. A method of producing a biometric sensor, which comprises the steps of:

providing a wafer having sensor chips with connecting contacts;

applying conductive bumps to the connecting contacts of the sensor chips;

covering a front side of the wafer with a scratch protection covering, openings in the scratch protection covering being kept free by use of a masking in an area of the conductive bumps;

separating the sensor chips from one another;

applying an adhesive layer around a sensor field of a respective sensor chip, the adhesive layer having a thickness being matched to a height of conductive bumps such that, in a subsequent method step, a leak-tight connection between the sensor chip and a chip housing is created;

introducing the sensor chip into the chip housing, the chip housing having electrical connecting leads disposed one of in and on the chip housing; and carrying out simultaneously an adhesive bonding of the sensor chip to the chip housing and a making of contact between the conductive bumps and the electrical connecting leads belonging to the chip housing.

\* \* \* \* \*